United States Patent [19]
Connor et al.

[11] Patent Number: 6,162,830
[45] Date of Patent: Dec. 19, 2000

[54] BENZENESULFONAMIDE INHIBITORS OF PDE-IV AND THEIR THERAPEUTIC USE

[75] Inventors: David Thomas Connor, Ann Arbor; Joseph Peter Menetski, Dexter, both of Mich.

[73] Assignee: Warner-Lambert Company, Morris Plains, N.J.

[21] Appl. No.: 09/485,252

[22] PCT Filed: Nov. 4, 1998

[86] PCT No.: PCT/US98/23482

§ 371 Date: Feb. 7, 2000

§ 102(e) Date: Feb. 7, 2000

[87] PCT Pub. No.: WO99/26616

PCT Pub. Date: Jun. 3, 1999

Related U.S. Application Data

[60] Provisional application No. 60/066,943, Nov. 25, 1997.

[51] Int. Cl.7 .................................................. A61K 31/18
[52] U.S. Cl. ......................... 514/604; 514/538; 514/523; 514/315; 514/427
[58] Field of Search .................................... 514/604, 523, 514/538, 315, 427

[56] References Cited

U.S. PATENT DOCUMENTS 5,283,352  2/1994  Backstrom et al. .................... 558/401

FOREIGN PATENT DOCUMENTS

| | | |
|---|---|---|
| 94/02465 | 2/1994 | WIPO . |
| 95/35283 | 12/1995 | WIPO . |
| 96/36595 | 11/1996 | WIPO . |
| 96/36596 | 11/1996 | WIPO . |
| 96/36611 | 11/1996 | WIPO . |
| 97/44322 | 11/1997 | WIPO . |

*Primary Examiner*—James H. Reamer
*Attorney, Agent, or Firm*—Charles W. Ashbrook

[57] ABSTRACT

The present invention provides compounds and pharmaceutical compositions thereof, and methods of using same in the treatment of diseases whose treatment benefits from the inhibition of phosphodiesterase (PDE-IV) or Tumor Necrosis Factor (TNF) including asthma, allergic diseases, rheumatoid arthritis, osteoarthritis, septic shock. The compounds provided by this invention have formula (I) wherein $R_1$, $R_2$, $R_3$, $R_4$ are as defined herein.

31 Claims, No Drawings

BENZENESULFONAMIDE INHIBITORS OF PDE-IV AND THEIR THERAPEUTIC USE

This application claims benefit of Provisional Appl. 60/066,943 filed Nov. 25, 1997.

FIELD OF THE INVENTION

The present invention relates to known and novel sulfonamide compounds and pharmaceutically acceptable salts thereof, processes for their production, formulation, and use as pharmaceuticals in the treatment of asthma, allergic diseases, rheumatoid arthritis, osteoarthritis, septic shock, and other diseases treatable by the inhibition of phosphodiesterase-IV (PDE-IV) or Tumour Necrosis Factor (TNF).

SUMMARY OF THE RELATED ART

Phosphodiesterases regulate cyclic AMP concentrations. Phosphodiesterase IV has been demonstrated to be a principal regulator of cyclic AMP in respiratory smooth muscle and inflammatory cells (Trophy and Creslinski, *Molecular Pharmacology* 37:206 (1990); Dent, et al.: *British Journal of Pharmacology*, 90:163 (1990)). Inhibitors of PDE-IV have been implicated as being bronchodilators and asthma-prophylactic agents and as agents for inhibiting eosinophil accumulation and the function of eosinophils (for example, Giembycz and Dent, *Clinical and Experimental Allergy*, 22:237 (1992)) and for treating other diseases and conditions characterized by, or having an etiology including, morbid eosinophil accumulation. Inhibitors of phosphodiesterase-IV are also implicated in treating inflammatory diseases, proliferative skin disease and conditions associated with cerebral metabolic inhibition.

Excessive or unregulated production of Tumour Necrosis Factor (TNF), a serum glycoprotein, has been implicated in mediating, or exacerbating a number of diseases including, rheumatoid arthritis, rheumatoid spondylitis, osteoarthritis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, and myalgias due to infection, such as influenza, cachexia secondary to acquired immune deficiency syndrome (AIDS), AIDS, ARC (AIDS-related complex), keloid formation, scar tissue formation, Crohn's disease, ulcerative colitis, or pyresis, in addition to a number of autoimmune diseases, such as multiple sclerosis, autoimmune diabetes, and systemic lupus erythematosis.

TNF has also been implicated in various roles with other viral infections, such as the cytomegalovirus (CMV), influenza virus, adenovirus, and the herpes virus.

TNF is also associated with yeast and fungal infections. Specifically *Candida albicans* has been shown to induce TNF production in vitro in human monocytes and natural killer cells [see Riipi, et al., *Infection and Immunity*, 58(9):2750–54 (1990); and Jafari, et al., *Journal of Infectious Diseases*, 162:211–214 (1990)].

Benzenesulfonamide inhibitors of PDE-IV and TNF of the general formula:

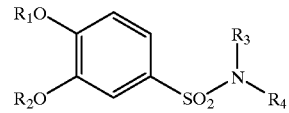

have been disclosed:

International Patent Application WO 94/02465 discloses, inter alia, compounds of Formula I wherein $R_1$ represents alkyl; $R_2$ represents alkyl or cycloalkyl; $R_3$ represents H; and $R_4$ represents aryl or heteroaryl.

International Patent Application WO 95/35283 discloses compounds of Formula I wherein $R_1$ represents H or alkyl; $R_2$ represents optionally substituted heterocycloaliphatic or an optionally substituted moncyclic or bicyclic aryl group; $R_3$ is alkyl; and $R_4$ represents $(Alk)_t(X)_n Ar$, where Alk is an optionally substituted straight or branched alkyl chain, optionally interrupted by an atom or group X, where X is —O—, —S(O)$_m$—, or —N($R^b$)—, (where $R^b$ is a hydrogen atom or an optionally substituted alkyl group, and m is zero or an integer of value 1 or 2), and Ar is a monocyclic or bicyclic aryl group optionally containing one or more heteroatoms selected from oxygen, sulfur, or nitrogen atoms.

International Patent Application WO 96/36611 discloses compounds of Formula I, wherein $R_1$ represents $C_{1-3}$ alkyl optionally substituted with halogen; $R_2$ represents optionally substituted $C_{1-6}$ alkyl, or optionally substituted cycloalkyl; $R_3$ and $R_4$, together with nitrogen atom to which they are attached, form a 6- or 7-membered heterocyclic ring, to which ring is fused a carbocyclic, aryl, heteroaryl, or heterocyclic optionally substituted ring.

International Patent Application WO 96/36595 discloses compounds of Formula I, wherein $R_1$ represents $C_{1-3}$ alkyl optionally substituted with halogen; $R_2$ represents optionally substituted $C_{1-6}$ alkyl, or optionally substituted cycloalkyl; $R_3$ represents arylalkyl, heteroarylalkyl, heterocycloalkyl, $COR_5$, $S(O)_m R_5$ or $C_{1-6}$ optionally substituted alkyl (where $R_5$ represents optionally substituted aryl, heteroaryl, heterocyclo or $C_{1-6}$ alkyl, and m is zero, 1, or 2); and $R_4$ represents arylalkyl, heteroarylalkyl, or heterocycloalkyl.

International Patent Application WO 96/36596 discloses compounds of Formula I, wherein $R_1$ represents $C_{1-3}$ alkyl optionally substituted with halogen; $R_2$ represents optionally substituted $C_{1-6}$ alkyl, or optionally substituted cycloalkyl; $R_3$ represents H; arylalkyl, hetarylalkyl, heterocycloalkyl, $COR_5$, $S(O)_m R_5$, or $C_{1-6}$ optionally substituted alkyl (where $R_5$ represents optionally substituted aryl, heteroaryl, heterocyclo, or $C_{1-6}$ alkyl, and m is zero, 1, or 2); and $R_4$ represents a 5- or 6-membered optionally substituted carbocyclic, or heterocyclic ring, to which ring is fused an optionally substituted aryl, heteroaryl, carbocyclic or heterocyclic ring.

Despite the progress that has been made, there remains a need for compounds that are useful in treating TNF-mediated or PDE-IV-mediated disease states in mammals who are in need of such treatment. This need is greatest for compounds that are relatively simple structurally, and, therefore, are simpler to synthesize, and, consequently, less expensive to manufacture.

SUMMARY OF THE INVENTION

The present invention comprises compounds of Formula I that have the ability to treat disease states associated with proteins that mediate cellular activity, for example, by inhibiting TNF and/or by inhibiting PDE-IV. The present invention provides compounds that are simpler and relatively easier to produce than previously described compounds that inhibit PDE-IV or TNF. According to the invention, the compounds are of Formula I:

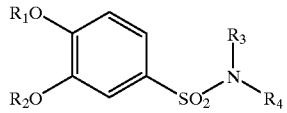

wherein
$R_1$ and $R_2$ represent lower alkyl or cycloalkyl;
$R_3$ and $R_4$ independently represent $C_1$–$C_4$ alkyl, cycloalkyl, $C_2$–$C_4$ alkylenes having one double bond, $C_2$–$C_4$ alkylynes having one triple bond, $(CH_2)_nCO$ $(CH_2)_mCH_3$, $(CH_2)_pCN$, $(CH_2)_pCO_2Me$, or taken together with the nitrogen atom to which they are attached, form a 3- to 10-membered ring; and pharmaceutically acceptable salts thereof;
n and m are independently 0 to 3; and
p is 1 to 3.

The invention also comprises pharmaceutical compositions and methods of using the compounds for inhibition of PDE-IV and TNF, in vitro and in vivo.

The foregoing merely summarizes certain aspects of the present invention and is not intended, nor should it be construed, as limiting the invention in any manner. All patents and other publications referenced herein are hereby incorporated by reference in their entirety.

DETAILED DESCRIPTION OF THE INVENTION

The present invention comprises TNF and PDE-IV inhibitors of Formula I that are useful in vitro and in vivo. In vitro, these compounds are useful as research tools for inhibiting TNF and PDE-IV to study effects of such inhibition on cellular and systemic biological processes. In vivo, these compounds are useful for the treatment of disease states associated with TNF and PDE-IV. The present invention provides compounds that are simpler and relatively easier to produce than previously described compounds that inhibit PDE-IV or TNF. According to the invention, the compounds are of Formula I:

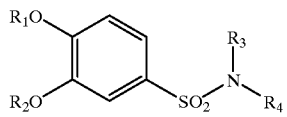

wherein
$R_1$ and $R_2$ represent lower alkyl or cycloalkyl;
$R_3$ and $R_4$ independently represent $C_{1-4}$ alkyl, cycloalkyl, $C_{2-4}$ alkylene, $C_{2-4}$ alkylyne, $(CH_2)_nCO(CH_2)_mCH_3$, $(CH_2)_pCN$, $(CH_2)_pCO_2Me$, or taken together with nitrogen atom to which they are attached, form a 3- to 10-membered ring;
n and m are 0 to 3;

p is 1 to 3;
and pharmaceutically acceptable salts thereof.

Preferred compounds of the invention include those in which $R_1$ and $R_2$ are ethyl; $R_3$ is $C_{1-4}$ alkyl, and $R_4$ is a $C_{2-4}$ alkylene with one double bond.

When used herein, the terms "alkyl" and "lower alkyl," whether used alone or when used as a part of another group, mean a straight or branched chain hydrocarbon having from 1 to 4 carbon atoms. Alkylene means an alkyl group containing at least one double bond. Alkylyne means an alkyl group containing at least one triple bond. Cycloalkyl includes a nonaromatic cyclic or multicyclic ring system of 3 to 10 carbon atoms.

"TNF mediated disease or disease states" means any and all disease states in which TNF plays a role, either by production of TNF itself, or by TNF causing another cytokine to be released, such as, but not limited to, IL-1 or IL-6. A disease state in which IL-1, for instance, is a major component and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention, and thus are herein referred to collectively as "TNF" unless specifically delineated otherwise.

The viruses contemplated for treatment herein are those that produce TNF as a result of infection, or those that are sensitive to inhibition, such as by decreased replication, directly or indirectly, by the TNF inhibitors of Formula I. Such viruses include, but are not limited to HIV-1, HIV-2, and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal afflicted with a human immunodeficiency virus (HIV), which comprises administering to such mammal an effective TNF inhibiting amount of a compound of Formula I or a pharmaceutically acceptable salt thereof.

The compounds of this invention may also be used in association with the veterinary treatment of animals, other than humans, in need of inhibition of TNF production. TNF mediated diseases for treatment. therapeutically or prophylactically; in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus, and other lentiviruses.

The compounds of this invention are also useful in treating parasite, yeast, and fungal infection, where such yeast and fungi are sensitive to up-regulation by TNF or will elicit TNF production in vivo. A preferred disease state for treatment is fungal meningitis.

This invention also comprises a method for mediating or inhibiting the enzymatic activity or catalytic activity of PDE-IV in a mammal in need thereof and for inhibiting the production of TNF in a mammal in need thereof, which comprises administering to said mammal an effective PDE-IV or TNF-inhibiting amount of a compound of Formula I or a pharmaceutically acceptable salt thereof.

PDE-IV inhibitors are useful in the treatment of a variety of allergic and inflammatory diseases, including: asthma, chronic bronchitis, atopic dermatitis, urticaria, allergic rhinitis, allergic conjunctivitis, venal conjunctivitis, inflammation of the eye, allergic responses in the eye, eosinophilic granuloma, psoriasis, rheumatoid arthritis, gouty arthritis and other arthritic conditions, ulcerative colitis, Crohn's disease, adult respiratory distress syndrome, diabetes insipidus, keratosis, atopic dermatitis, atopic eczema, cerebral senility, multi-infarct dementia, senile dementia, memory impairment associated with Parkinson's disease, depression, cardiac arrest, stroke, and intermittent claudication. Additionally, PDE-IV inhibitors could have utility as gastroprotectants.

A preferred embodiment of the therapeutic methods of the present invention is the treatment of asthma.

The compounds of Formula I are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90%, and still more preferably 95%.

A process for the preparation of a compound of Formula Ia comprises reaction of an appropriate sulfonyl chloride of Formula II with a suitable amine of Formula III.

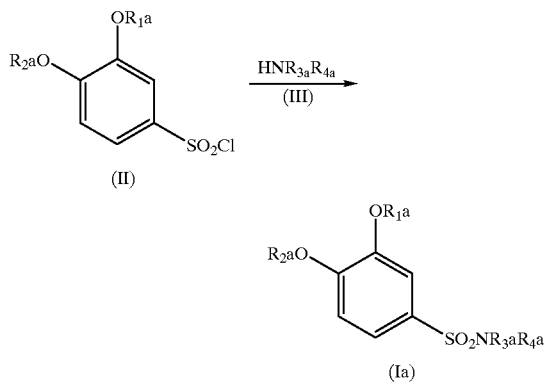

wherein $R_{1a}$ represents $R_1$ as defined in relation to Formula I or a group convertible to $R_1$ and $R_{2a}$–$R_{4a}$ similarly represent $R_2$–$R_4$ or groups convertible to $R_2$–$R_4$, respectively; and thereafter, if required, converting any group $R_{1a}$ to $R_1$ and/or $R_{2a}$ to $R_2$ and/or $R_{3a}$ to $R_3$ and/or $R_{4a}$ to $R_4$.

The reaction of a sulfonyl chloride of Formula II with a compound of Formula III may be carried out under any suitable conditions known to those skilled in the art. When compound (iii) is an amine, favorably the reaction is carried out in the presence of a suitable base, for example an amine such as triethylamine, preferably in an appropriate solvent such as dichloromethane.

Alternatively, the substituents $R_{3a}$ and $R_{4a}$ can be added sequentially in a 2-step process. This alternative process for preparing a compound of Formula Ia comprises reaction of an appropriate sulfonyl chloride of Formula II with a suitable primary amine of Formula VI, and reaction of the resulting sulfonamide VII with a compound of Formula VIII (e.g., an alkyl halide where X is a leaving group such as chloro or bromo) and a base such as sodium hydride.

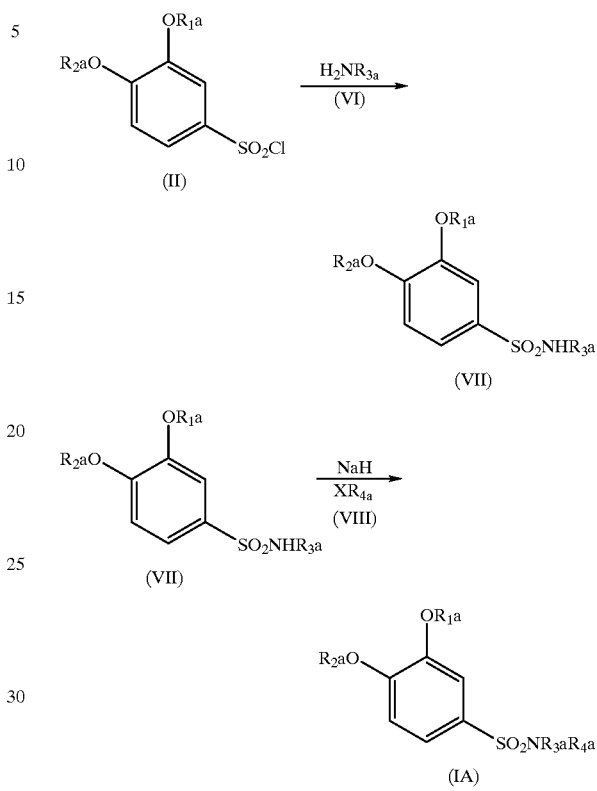

Sulfonyl chlorides of Formula II are either commercially available or are prepared using standard procedures known to those skilled in the art. For example, a sulfonyl chloride is conveniently prepared from the appropriate sulfonic acid (IV) by reaction with a suitable chlorinating agent such as thionyl chloride or oxalyl chloride. An appropriate sulfonic acid may be prepared from a compound of formula (v) by sulfonylation using an appropriate sulfonylating agent, for example chlorosulfonic acid. Alternatively, a sulfonyl chloride of Formula II may be prepared directly from a compound of Formula V by using excess chlorosulfonic acid. Compounds of Formula V are either commercially available or may be prepared by standard procedure known to those skilled in the art.

Compounds of Formula II, III, IV, V VI, and VII are either commercially available, previously described compounds, or are prepared using standard procedures known to those skilled in the art.

In some cases compounds of Formula III will be amides (due to the inclusion of a catbonyl group in $R_3$, $R_4$, $R_{3a}$, or $R_{4a}$), and in these cases their reaction with a sulphonyl chloride will require a stronger base, such as sodium hydride and a polar solvent favorably N,N-dimethylformamide.

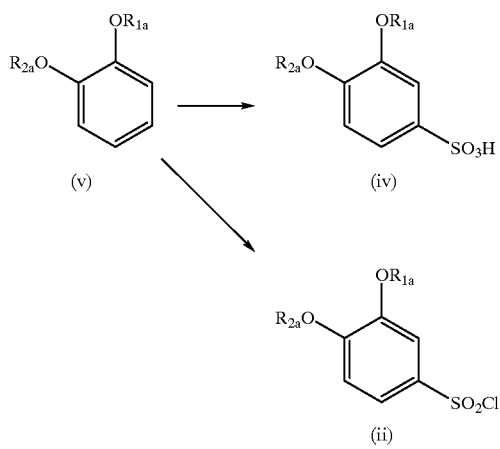

The present invention additionally provides a pharmaceutical composition comprising a compound of Formula I, or where appropriate a pharmaceutically acceptable salt thereof and/or a pharmaceutically acceptable solvate thereof, and a pharmaceutically acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, or parenteral administration, or through the respiratory tract. Preparations may be designed to give slow and controlled release of the active ingredient.

The term "parenteral" as used herein includes subcutaneous injections, intravenous, intramuscular, intrasternal injection, or infusion techniques. In addition to the treatment of warm-blooded animals such as mice, rats, horses, cattle, sheep, dogs, cats, etc., the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions, or suspensions. Topical formulations are also envisaged where appropriate, for example transdermal patch systems, lotions, and creams.

In order to obtain consistency of administration, it is preferred that a composition of the invention is in the form of a unit dose.

Unit dose presentation forms for oral administration may be tablets and capsules and may contain conventional excipients such as binding agents, for example acacia, gelatin, sorbitol, tragacanth, or polyvinylpyrrolidone. Fillers may be utilized, for example microcrystalline cellulose, lactose, sugar, maize-starch, calcium phosphate, sorbitol, or glycine. Tabletting lubricants can be employed, for example magnesium stearate, as well as disintegrants, for example starch, polyvinylpyrrolidone, sodium starch glycollate, or microcrystalline cellulose; and pharmaceutically acceptable wetting agents such as sodium lauryl sulfate.

The solid oral compositions may be prepared by conventional methods of blending, filling, tabletting or the like. Repeated blending operations may be used to distribute the active agent throughout those compositions employing large quantities of fillers.

Such operations are, of course, conventional in the art. The tablets may be coated according to methods well-known in normal pharmaceutical practice, in particular with an enteric coating.

Oral liquid preparations may be in the form of, for example emulsions, syrups or elixirs, or may be presented as a dry product for reconstitution with water or other suitable vehicle before use. Such liquid preparations may contain conventional additives such as suspending agents, for example sorbitol, methyl cellulose, gelatin, hydroxyethylcellulose, carboxymethylcellulose, aluminum stearate gel, hydrogenated edible fats, emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired, conventional flavouring or coloring agents.

Compositions may also be prepared for administration to the respiratory tract, for instance as a snuff or an aerosol or solution for a nebuliser, or as a microfine powder for insufflation, alone or in combination with an inert carrier such as lactose. In such a case, the particles of active compound suitably have diameters of less than 50 microns, such as from 0.1 to 50 microns, preferably less than 10 microns, for example from 1 to 10 microns, 1 to 5 microns or from 2 to 5 microns. Where appropriate, small amounts of other antiasthmatics and bronchodilators, for example sympathomimetic amines such as isoprenaline, isoetharine, salbutamol, phenylephrine, and ephedrine, or corticosteroids such as prednisolone and adrenal stimulants such as ACTH, may be included.

For parenteral administration, fluid unit dosage forms are prepared utilizing a compound of Formula I and a sterile vehicle, and, depending on the concentration used, can be either suspended or dissolved in the vehicle. In preparing solutions, the active compound can be dissolved in water for injection and filter sterilized before filling into a suitable vial or ampoule and sealing.

Advantageously, adjuvants such as a local anaesthetic, a preservative, and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10% to 60% by weight, of the active material, depending on the method of administration.

Compounds of Formula I, or if appropriate a pharmaceutically acceptable salt thereof and/or a pharmaceutically acceptable solvate thereof, may also be administered as a topical formulation in combination with conventional topical excipients.

Topical formulations may be presented as, for instance, ointments, creams, or lotions, impregnated dressings, gels, gel sticks, sprays and aerosols, and may contain appropriate conventional additives such as preservatives. solvents to assist drug penetration, and emollients in ointments and creams. The formulations may contain compatible conventional carriers, such as cream or ointment bases and ethanol or oleyl alcohol for lotions.

Suitable cream, lotion, gel, stick, ointment, and spray aerosol formulations that may be used for compounds of Formula I (or if appropriate, a pharmaceutically acceptable salt or solvate thereof) are conventional formulations well-known in the art, for example, as described in standard text books such as Harry's Cosmeticology published by Leonard Hill Books, Remington's Pharmaceutical Sciences, and the British and U.S. Pharmacopoeias.

The compound of Formula I, or if appropriate, a pharmaceutically acceptable salt or solvate thereof will compromise from about 0.5% to about 80% by weight of the formulation, typically from about 1% to about 50% and ideally about 5% to about 20%.

The dose of the compound used in the treatment of the invention will vary in the usual way with the seriousness of the disorders, the weight of the sufferer, and the relative efficacy of the compound. However, as a general guide suitable unit doses may be 0.1 to 500 mg, such as 0.5 to 200, 0.5 to 100, or 0.5 to 10 mg, for example 0.5, 1, 2, 3, 4, or 5 mg; and such unit doses may be administered more than once a day, for example 2, 3, 4, 5, or 6 times a day, but preferably 1 or 2 times per day, so that the total daily dosage for a 70 kg adult is in the range of about 0.1 to about 10.0 mg/kg/day, such as 0.1 to 8.0 mg/kg/day, for example 1 or 2 mg/kg/day, and such therapy may extend for a number of weeks or months.

When used herein, the term "pharmaceutically acceptable" encompasses materials suitable for both human and veterinary use.

The following examples are provided for illustrative purposes only and are not intended, nor should they be construed, as limiting the invention in any manner. Those skilled in the art will appreciate that modifications and variations of the following examples can be made without exceeding the spirit or scope of the present invention and claims.

EXAMPLE 1

N-(2-Propynyl)-N-methyl-3,4-dimethoxybenzenesulfonamide: mp 104–105° C.

3,4-Dimethoxybenzene sulfonyl chloride (11.8 g) in tetrahydrofuran (100 mL) is added slowly with stirring to a mixture of N-methylpropargylamine (3.5 g), triethylamine (5.05 g), and tetrahydrofuran (100 mL). The resulting mixture is refluxed 1 hour, cooled, filtered, and evaporated to dryness. The residue is treated with water, filtered, washed with water, and dried. Recrystallization from ethanol gave 8.7 g of the title product.

The following compounds were prepared by the same method from 3,4-dimethoxybenzene sulfonyl chloride and the corresponding amine:

EXAMPLE 2
N,N-Dimethyl-3,4-dimethoxybenzenesulfonamide: mp 114–115° C.

EXAMPLE 3
N,N-Diethyl-3,4-dimethoxybenzenesulfonamide: mp 96–98° C.

EXAMPLE 4
N,N-Dipropyl-3,4-dimethoxybenzenesulfonamide: mp 46–47° C.

EXAMPLE 5
N,N-Di-(2-propenyl)-3,4-dimethoxybenzenesulfonamide: mp 68–69° C.

EXAMPLE 6
N,N-Dimethyl-3,4-diethoxybenzenesulfonamide: mp 100–102° C.

EXAMPLE 7
N-(3,4-dimethoxybenzenesulfonyl)piperidine: mp 99–100° C.

EXAMPLE 8
N-(3,4-dimethoxybenzenesulfonyl)pyrrolidine: mp 129–130° C.

EXAMPLE 9
N-(3,4-dimethoxybenzenesulfonyl)cyclohexylamine: mp 99–100° C.

EXAMPLE 10
N-(2-Propynyl)-N-methyl-3,4-diethoxybenzenesulfonamide: mp 69–70° C.

EXAMPLE 11
N-Ethyl-N-methyl-3,4-dimethoxybenzenesulfonamide: mp 71–72° C.

Sodium hydride (2.1 g) is added with stirring to a solution of 3,4-dimethoxybenzenemethylsulfonamide (11.55 g) in dimethylformamide (100 mL). The mixture is cooled to 15° C., and ethyl iodide (7.8 g) is added with stirring. The solution is stirred at room temperature for 5 hours, heated on a steam bath for 30 minutes, and concentrated under vacuum. The residue is triturated with water, filtered, washed with water, and dried to give 7.52 g of the title product.

The following compounds are prepared by the same method from 3,4-dimethoxybenzenemethylsulfonamide or from 3,4-diethoxybenzenmethylsulfonamide and the corresponding $XR_{4a}$ halide:

EXAMPLE 12
N-Propyl-N-methyl-3,4-dimethoxybenzenesulfonamide: mp 84–85° C.

EXAMPLE 13
N-Butyl-N-methyl-3,4-dimethoxybenzenesulfonamide: mp 79–80° C.

EXAMPLE 14
N-(2-Methylethyl)-N-methyl-3,4-dimethoxybenzenesulfonamide: mp 93–94° C.

EXAMPLE 15
N-(2-Propenyl)-N-methyl-3,4-dimethoxybenzenesulfonamide: mp 44–46° C.

EXAMPLE 16
N-(2-Butenyl)-N-methyl-3,4-dimethoxybenzenesulfonamide: mp 93–94° C.

EXAMPLE 17
N-(2-Propenyl)-N-methyl-3,4-diethoxybenzenesulfonamide: mp 61–62° C.

EXAMPLE 18
N-(3-Propylnitrile)-N-methyl-3,4-dimethoxybenzenesulfonamide: mp 90–92° C.

EXAMPLE 19
N-(4-Butylnitrile)-N-methyl-3,4-dimethoxybenzenesulfonamide: mp 50–52° C.

EXAMPLE 20
N-Methyl-N-(2-Oxopropyl)-3,4-dimethoxybenzenesulfonamide: mp 95–96° C.

EXAMPLE 21
N-Methyl-N-(3-Oxopentyl)-3,4-dimethoxybenzenesulfonamide: mp 94–96° C.

EXAMPLE 22
Ethyl N-(methylenecarboxy)-N-methyl-3,4-dimethoxybenzenesulfonamide: mp 94–96° C.

EXAMPLE 23
N-(methylenenitrile)-N-methyl-3,4-dimethoxybenzenesulfonamide: mp 101–103° C.

EXAMPLE 24
N-(methylenenitrile)-N-methyl-3,4-diethoxybenzenesulfonamide: mp 95–97° C.

PDE-IV Assay Procedure

Representative compounds to be tested were diluted in 96-well plates. The compounds were either received as a 10 mM stock solution in DMSO, or as a solid which was resuspended to a concentration of 10 mM in DMSO. The compounds were initially tested at 10, 3, 1, 0.3, and 0.1 μM to calculate an $IC_{50}$. In some cases, plates containing diluted compounds were frozen before being assayed. In these cases, the plates were thawed for 15 minutes at 37° C. and agitated before proceeding.

Two microliters of the diluted compounds on Rolipram were spotted into an assay plate. Ninety-eight microliters of reaction mixture containing PDE-IV enzyme were added to each well. The plate was then agitated for 2 minutes at a setting of 3.5 on a vortex and incubated for 1 hour at 37° C. The reaction was terminated with 50 μl of 0.5X SPA beads, and the reaction tray was allowed to incubate at room temperature for 20 minutes before radioactivity was measured using standard instrumentation.

The reaction mixture contained 35.2 mM Tris pH 8.0, 9.4 mM $MgCl_2$, 4 mM β-mercapotoethanol, 200 nM cAMP, 8 nM $^3$H-cAMP, 2% DMSO 1% U937 lysate (from ABS). The reaction mixture was prepared by adding 87 Ml $H_2O$ to 10 mL 10X Assay Buffer, 40 μL 1 μCi/μL $^3$H-cAMP, 20 μL 1 mM cAMP (cAMP stock made fresh each time), and 1 mL U937 cell lysate. 10X assay buffer was prepared by mixing 400 mM Tris Base with 400 mM Tris HCl to pH 8.0, adding to 100 mL of this Tris buffer solution, 1.017 g $MgCl_2$, 319 μL μ-mercaptoethanol. 0.5X SPA beads was prepared by adding 500 mg beads to 56 mL $H_2O$ for a final concentration of 8.9 mg/mL beads and 9 mM zinc sulfate.

The results are summarized below.

| Table of PDE-IV Inhibition | |
|---|---|
| Example | PDE IV ($IC_{50}$ μM) |
| 4 | 0.46 |
| 5 | 0.45 |
| 6 | 0.28 |
| 7 | 3.6 |
| 8 | 3.2 |
| 9 | 2.2 |
| 10 | 0.17 |
| 11 | 0.7 |
| 12 | 0.47 |
| 15 | 0.66 |
| 16 | 1.56 |
| 17 | 0.02 |
| 23 | 1.76 |

What is claimed is:

1. A method of inhibiting PDE-IV or TNF comprising contacting a cell with a compound of the general formula

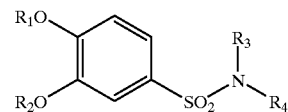

wherein
$R_1$ and $R_2$ represent $C_1$–$C_4$ alkyl or $C_3$–$C_{10}$ cycloalkyl; $R_3$ and $R_4$ independently represent $C_{1-4}$ alkyl, cycloalkyl, $C_2$–$C_4$ alkylenes having one double bond, $C_2$–$C_4$ alkylynes having one triple bond, $(CH_2)_nCO(CH_2)_mCH_3$, $(CH_2)_pCN$, $(CH_2)_pCO_2Me$, or taken together with nitrogen atom to which they are attached, form a 3- to 10-membered ring;
n and m are 0 to 3;
p is 1 to 3;
and pharmaceutically acceptable salts thereof.

2. A method according to claim 1, wherein $R_1$ and $R_2$ are independently $C_1$–$C_4$ alkyl.

3. A method according to claim 1, wherein $R_1$ and $R_2$ are ethyl.

4. A method according to claim 1, wherein $R_3$ and $R_4$ independently represent $C_1$–$C_4$ alkyl, $C_2$–$C_4$ alkylenes having one double bond, or $C_2$–$C_4$ alkylynes having one triple bond.

5. A method according to claim 2, wherein $R_3$ and $R_4$ independently represent $C_1$–$C_4$ alkyl, $C_2$–$C_4$ alkylenes having one double bond, or $C_2$–$C_4$ alkylynes having one triple bond.

6. A method according to claim 3, wherein $R_3$ and $R_4$ independently represent $C_2$–$C_4$ alkyl, $C_2$–$C_4$ alkylenes having one double bond, or $C_1$–$C_4$ alkylynes having one triple bond.

7. A method according to claim 1, selected from the group consisting of
N-(2-Propynyl)-N-methyl-3,4-dimethoxybenzenesulfonamide,
N,N-Dimethyl-3,4-dimethoxybenzenesulfonamide,
N,N-Diethyl-3,4-dimethoxybenzenesulfonamide,
N,N-Dipropyl-3,4-dimethoxybenzenesulfonamide, N,N-Di-(2-propenyl)-3,4-dimethoxybenzenesulfonamide,
N,N-Dimethyl-3,4-diethoxybenzenesulfonamide,
N-(3,4-dimethoxybenzenesulfonyl)piperidine,
N-(3,4-dimethoxybenzenesulfonyl)pyrrolidine,
N-(3,4-dimethoxybenzenesulfonyl)cyclohexylamine,
N-(2-Propynyl)-N-methyl-3,4-diethoxybenzenesulfonamide,
N-Ethyl-N-methyl-3,4-dimethoxybenzenesulfonamide,
N-Propynl)-N-methyl-3,4-dimethoxybenzenesulfonamide,
N-Butyl-N-methyl-3,4-dimethoxybenzenesulfonamide,
N-(2-Methylethyl)-N-methyl-3,4-dimethoxybenzenesulfonamide,
N-(2-Propenyl)-N-methyl-3,4-dimethoxybenzenesulfonamide,
N-(2-Butenyl)-N-methyl-3,4-dimethoxybenzenesulfonamide,
N-(2-Propenyl)-N-methyl-3,4-diethoxybenzenesulfonamide,
N-(3-Propylnitrile)-N-methyl-3,4-dimethoxybenzenesulfonamide,
N-(4-Butylnitrile)-N-methyl-3,4-dimethoxybenzenesulfonamide,
N-Methyl-N-(2-Oxopropyl)-3,4-dimethoxybenzenesulfonamide,
N-Methyl-N-(3-Oxopentyl)-3,4-dimethoxybenzenesulfonamide, Ethyl
N-(methylenecarboxy)-N-methyl-3,4-dimethoxybenzenesulfonamide,
N-(methylenenitrile)-N-methyl-3,4-dimethoxybenzenesulfonamide, and
N-(methylenenitrile)-N-methyl-3,4-diethoxybenzenesulfonamide.

8. A pharmaceutical composition comprising a compound of the general formula:

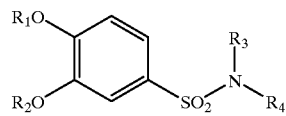

wherein
$R_1$ and $R_2$ represent lower alkyl or cycloalkyl;
$R_3$ and $R_4$ independently represent $C_1$–$C_4$ alkyl, cycloalkyl, $C_2$–$C_4$ alkylenes having one double bond, $C_2$–$C_4$ alkylynes having one triple bond, $(CH_2)_nCO(CH_2)_mCH_3$, $(CH_2)_pCN$, $(CH_2)_pCO_2Me$, or taken together with nitrogen atom to which they are attached, form a 3- to 10-membered ring;
n and m are 0 to 3;
p is 1 to 3;
or pharmaceutically acceptable salts thereof and a pharmaceutically acceptable carrier.

9. A pharmaceutical composition according to claim 8, wherein $R_1$ and $R_2$ are independently $C_1$–$C_4$ alkyl.

10. A pharmaceutical composition according to claim 8, wherein $R_1$ and $R_2$ are ethyl.

11. A pharmaceutical composition according to claim 8, wherein $R_3$ and $R_4$ independently represent $C_1$–$C_4$ alkyl, $C_2$–$C_4$ alkylenes having one double bond, or $C_2$–$C_4$ alkylynes having one triple bond.

12. A pharmaceutical composition according to claim 9, wherein $R_3$ and $R_4$ independently represent $C_1$–$C_4$ alkyl, $C_2$–$C_4$ alkylenes having one double bond, or $C_2$–$C_4$ alkylynes having one triple bond.

13. A pharmaceutical composition according to claim 10, wherein $R_3$ and $R_4$ independently represent $C_1$–$C_4$ alkyl, $C_2$–$C_4$ alkylenes having 1 double bond, or $C_2$–$C_4$ alkylynes having 1 triple bond.

14. A pharmaceutical composition according to claim 8, comprising a compound selected from the group consisting of
N-(2-Propynyl)-N-methyl-3,4-dimethoxybenzenesulfonamide,
N,N-Dimethyl-3,4-dimethoxybenzenesulfonamide,
N,N-Diethyl-3,4-dimethoxybenzenesulfonamide,
N,N-Dipropyl-3,4-dimethoxybenzenesulfonamide,
N,N-Di-(2-propenyl)-3,4-dimethoxybenzenesulfonamide,
N,N-Dimethyl-3,4-diethoxybenzenesulfonamide,
N-(3,4-dimethoxybenzenesulfonyl)piperidine,
N-(3,4-dimethoxybenzenesulfonyl)pyrrolidine,
N-(3,4-dimethoxybenzenesulfonyl)cyclohexylamine,
N-(2-Propynyl)-N-methyl-3,4-diethoxybenzenesulfonamide,
N-Ethyl-N-methyl-3,4-dimethoxybenzenesulfonamide,
N-Propyl-N-methyl-3,4-dimethoxybenzenesulfonamide,
N-Butyl-N-methyl-3,4-dimethoxybenzenesulfonamide,
N-(2-Methylethyl)-N-methyl-3,4-dimethoxybenzenesulfonamide,
N-(2-Propenyl)-N-methyl-3,4-dimethoxybenzenesulfonamide,
N-(2-Butenyl)-N-methyl-3,4-dimethoxybenzenesulfonamide,
N-(2-Propenyl)-N-methyl-3,4-diethoxybenzenesulfonamide,
N-(3-Propylnitrile)-N-methyl-3,4-dimethoxybenzenesulfonamide,
N-(4-Butylnitrile)-N-methyl-3,4-dimethoxybenzenesulfonamide,
N-Methyl-N-(2-Oxopropyl)-3,4-dimethoxybenzenesulfonamide,
N-Methyl-N-(3-Oxopentyl)-3,4-dimethoxybenzenesulfonamide,
Ethyl N-(methylenecarboxy)-N-methyl-3,4-dimethoxybenzenesulfonamide,
N-(methylenenitrile)-N-methyl-3,4-dimethoxybenzenesulfonamide, and
N-(methylenenitrile)-N-methyl-3,4-diethoxybenzenesulfonamide.

15. A method for treating a disease state associated with a function of PDE-IV, eosinophil accumulation or a function of the eosinophil, comprising administering to a patient suffering from said disease an effective amount of a pharmaceutical composition according to claim 8.

16. A method for treating a disease state associated with a function of PDE-IV, eosinophil accumulation or a function of the eosinophil, comprising administering to a patient suffering from said disease an effective amount of a pharmaceutical composition according to claim 11.

17. A method for treating a disease state associated with a function of PDE-IV, eosinophil accumulation or a function of the eosinophil, comprising administering to a patient suffering from said disease an effective amount of a pharmaceutical composition according to claim 14.

18. The method of claim 15, wherein the disease state is a pathological condition capable of being modulated by inhibiting PDE-IV.

19. The method of claim 15, wherein the pathological condition is selected from asthma, chronic bronchitis, atopic dermatitis, urticaria, allergic rhinitis, allergic conjunctivitis, vernal conjunctivitis, inflammation of the eye, allergic responses in the eye, eosinophilic granuloma, psoriasis, rheumatoid arthritis, gouty arthritis and other arthritic conditions, ulcerative colitis, Crohn's disease, adult respiratory distress syndrome, diabetes insipidus, keratosis, atopic dermatitis, atopic eczema, cerebral senility, multiinfarct dementia, senile dementia, memory impairment associated with Parkinson's disease, depression, cardiac arrest, stroke, and intermittent claudication.

20. The method of claim 15, wherein the pathological condition is asthma.

21. A method for treating a disease state capable of being modulated by inhibiting TNF, comprising administering to a patient suffering from said disease an effective amount of a pharmaceutical composition according to claim 8.

22. A method for treating a disease state capable of being modulated by inhibiting TNF, comprising administering to a patient suffering from said disease an effective amount of a pharmaceutical composition according to claim 11.

23. A method for treating a disease state capable of being modulated by inhibiting TNF, comprising administering to a patient suffering from said disease an effective amount of a pharmaceutical composition according to claim 14.

24. The method of claim 21, wherein the disease state is an inflammatory disease or autoimmune disease.

25. The method of claim 21, wherein the disease state is selected from joint inflammation, arthritis, rheumatoid arthritis, rheumatoid spondylitis and osteoarthritis, sepsis, septic shock, endotoxic shock, gram negative sepsis, toxic shock syndrome, acute respiratory distress syndrome, cerebral malaria, chronic pulmonary inflammatory disease, silicosis, pulmonary sarcoidosis, asthma, bone resorption diseases, reperfusion injury, graft versus host reaction, allograft rejection, fever and myalgias due to infection, such as influenza, malaria, myalgias, HIV, AIDS, ARC, cachexia, keloid formation, scar tissue formation, Crohn's disease, ulcerative colitis, pyresis, systemic lupus erythematosis, multiple sclerosis, type 1 diabetes mellitus, psoriasis, Bechet's disease, anaphylactoid purpura nephritis, chronic glomerulonephritis, inflammatory bowel disease, and leukemia.

26. The method of claim 21, wherein the disease state is joint inflammation.

27. The method of claim 15 or 21, wherein the disease state is tardive dyskinesia.

28. The method of claim 21, wherein the disease state is a yeast or fungal infection.

29. A method for gastroprotection, comprising administering to a patient in need thereof an effective amount of a pharmaceutical composition according to claim 8.

30. A method for gastroprotection, comprising administering to a patient in need thereof an effective amount of a pharmaceutical composition according to claim 11.

31. A method for gastroprotection, comprising administering to a patient in need thereof an effective amount of a pharmaceutical composition according to claim 14.

\* \* \* \* \*